United States Patent

Abts et al.

[11] Patent Number: 4,580,444
[45] Date of Patent: Apr. 8, 1986

[54] ULTRASONIC DETERMINATION OF COMPONENT CONCENTRATIONS IN MULTI-COMPONENT FLUIDS

[75] Inventors: Leigh R. Abts, Barrington; Peter H. Dahl, Providence, both of R.I.

[73] Assignee: Micro Pure Systems, Inc., Warwick, R.I.

[21] Appl. No.: 578,831

[22] Filed: Feb. 10, 1984

[51] Int. Cl.⁴ ............................................. G01N 29/00
[52] U.S. Cl. ..................................... 73/61 R; 73/599
[58] Field of Search ................. 73/599, 61 R, 61.1 R, 73/19, 53

[56] References Cited

U.S. PATENT DOCUMENTS

| | | |
|---|---|---|
| 2,966,056 | 12/1960 | Heller ................................. 73/599 |
| 3,553,636 | 1/1971 | Baird ................................. 73/599 |
| 3,710,615 | 1/1973 | Johnson et al. .................... 73/61 R |
| 3,779,070 | 12/1973 | Cushman et al. ............... 73/432 PS |
| 3,816,773 | 6/1974 | Baldwin et al. .................... 73/61 R |
| 3,914,984 | 10/1975 | Wade ................................. 73/61 R |
| 4,015,464 | 5/1977 | Miller et al. ....................... 73/61 R |
| 4,112,773 | 9/1978 | Abts ................................. 73/61 R |
| 4,237,720 | 12/1980 | Abts ................................. 73/119 |
| 4,381,674 | 5/1983 | Abts ................................. 73/61 R |
| 4,412,451 | 11/1983 | Uusitalo et al. .................... 73/599 |
| 4,475,398 | 10/1974 | Tjornehoj et al. .................. 73/599 |
| 4,478,072 | 10/1974 | Brown ............................. 73/61 R |
| 4,527,420 | 7/1985 | Foote ............................... 73/61 R |
| 4,542,644 | 9/1985 | Claytor et al. ..................... 73/61 R |

Primary Examiner—Stewart J. Levy
Assistant Examiner—Hezron E. Williams

[57] ABSTRACT

A method of and apparatus for determining the concentration of oil in a recirculating fluid flow for an oil recovery system by detecting the forward-scattering of ultrasonic energy from oil droplets in the flow and comparing the detected information with forward-scattering measurements for flows with known concentrations of oil.

18 Claims, 3 Drawing Figures

ULTRASONIC DETERMINATION OF COMPONENT CONCENTRATIONS IN MULTI-COMPONENT FLUIDS

FIELD OF THE INVENTION

This invention relates to a method of and apparatus for determining the concentration of oil droplets in the recirculated flow of an oil recovery system.

BACKGROUND OF THE INVENTION

In secondary oil recovery systems, oil is recovered by pumping water into the ground through a secondary hole near the oil deposit. The water seeps through the ground, and as it is under pressure, the water forces the oil to the surface through a primary drill hole. This oil flow, however, will contain oil, water and solid particles. Most of the oil is separated from the rest of the flow at the surface, and the residual liquid is recirculated back into the ground through the secondary drill hole. The use of this residual water substantially reduces the amount of fresh or sea water which must be continually added while the system is in operation.

There is an important drawback to this method. Despite efforts to separate the oil and water at the surface, some oil will be carried back into the ground by the recirculated water. While the oil droplets do not adversely affect the system, other than by possibly confusing detectors trying to detect solid particles in the recirculated flow, the droplets could, if of sufficient quantity or size, put a great deal of oil back into the ground thereby defeating the purpose of the secondary oil recovery system to some degree.

SUMMARY OF THE INVENTION

We have discovered that discontinuities, particularly oil droplets, in a recirculatory flow for an oil recovery system can be identified and their concentration and size determined by using an ultrasonic transmitter to send pulses of ultrasonic energy into the flow whereby forward-scattering of the pulses from the droplets can be detected and measured to determine the concentration of oil in the flow.

In the preferred embodiment, a first transducer is mounted on a pipe carrying the recirculating water flow. A second transducer is also mounted on the pipe at an angle of at least 90° to the first. The ultrasonic pulses into the flow from the first transducer are forward-scattered by any oil droplets, but not by solid particles, and each forward-scattering is detected by the second transducer and counted. The number of such counts per unit volume determines the oil concentration, and the threshold level for the counter also gives an indication of minimum droplet size.

In another preferred embodiment, the arrangement of the first and second transducers is the same, but the second transducer is used to measure the amount of ultrasonic absorption or decibel level dropoff of the transmitted ultrasonic pulse. If oil droplets are present, the decibel level dropoff will record a gain because of the forward-scattering. The amount of this gain is used to determine the oil concentration.

PREFERRED EMBODIMENTS

We turn now to the structure and operation of the preferred embodiments, after first briefly describing the drawings.

DRAWINGS

STRUCTURE

Figure 1:
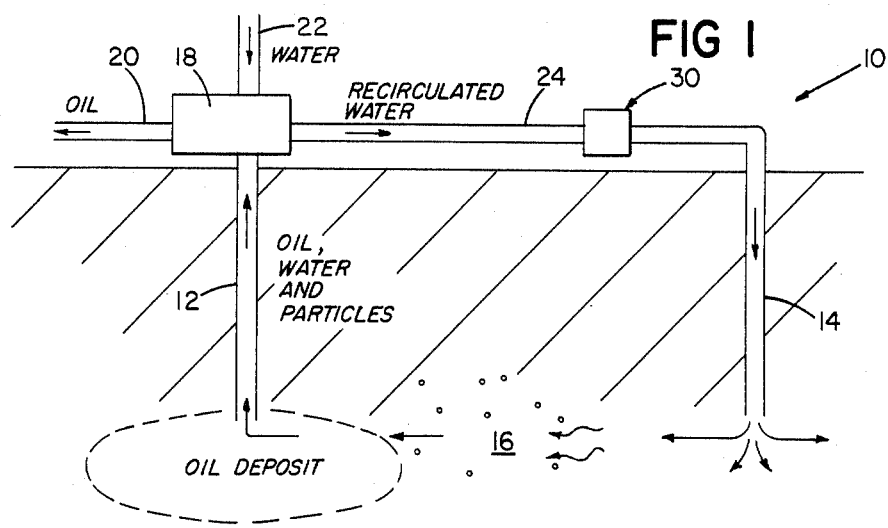
FIG. 1 is a cross-sectional view of an oil recovery system for use with this invention.

Referring to FIG. 1, there is shown a secondary oil recovery system at 10. System 10 comprises a primary drill hole 12 which extends into the oil deposit and a secondary drill hole 14, which is nearby. The lower end of secondary drill hole 14 is separated from the oil deposit by a ground seepage area 16.

The surface end of the primary drill hole 12 is connected to a separator unit 18. Separator unit 18 also has an oil output pipe 20, a water input pipe 22 and a recirculated water pipe 24. A detector 30, according to the invention herein, is disposed in the recirculated water pipe 24.

Figure 2:
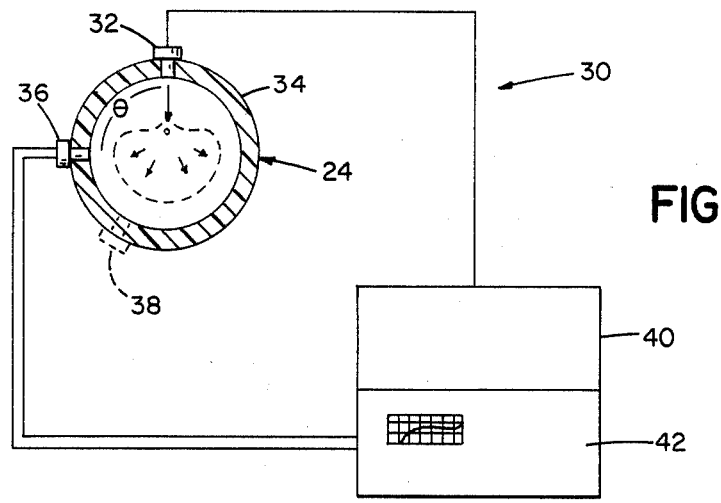
FIG. 2 is a block diagram of the preferred embodiment of the invention.

The detector 30 of the preferred embodiment is shown in FIG. 2. The detector 30 comprises a first ultrasonic transducer 32 disposed in a hole in a sidewall 34 of the recirculated water pipe 24. A second ultrasonic transducer 36 is disposed in a hole in the sidewall at an angle $\theta$ from the first transducer 32. In the preferred embodiment, the angle $\theta$ is 90°, which is the approximate minimum angle which can be used. An alternate location 38 for the second transducer, where $\theta$ is about 120°, is shown dotted in FIG. 2. The transducers 32, 36 are both 15 MHz transducers of the type disclosed in U.S. Pat. No. 4,365,515 and available from Micro Pure Systems, Inc. of Rhode Island, the assignee of this application.

The first transducer 32 is a transmitting transducer, and it is connected to a pulser-receiver 40. The second transducer 36 is a receiving transducer, and it is connected to a pulse counter 42. The pulser-receiver 40 and the pulse counter 42 are the MPH 1150 and the MP1100 respectively, both available from Micro Pure Systems, Inc.

OPERATION

In operation, water, preferably seawater, is drawn into the system 10 through inlet pipe 22, and this water is pumped through the recirculated water pipe 24 to the secondary drill hole 14. At the bottom of secondary drill hole 14, the water seeps into the ground under pressure. Some of this water passes through the ground seepage area 16 between the secondary drill hole 14 and the oil deposit. For the usual earth formation, the seepage area 16 in the vicinity of an oil deposit has small passageways of about $10\mu$ diameter. When the water reaches the oil deposit, the water pressure forces some of the oil up through the primary drill hole 12 and to the separator unit 18. This flow, however, also contains water and solid particles picked up by the water and oil. The separator unit 18 separates oil from the rest of the flow, and recovered oil is then pumped from outlet pipe 20. The remainder of the flow, which now is primarily water with some oil droplets and solid particles, is then fed back into the recirculated water pipe 24. The system 10, however, has a net water loss because water exits from the secondary drill hole in all directions and not all of it is recovered. Therefore, additional water, usually seawater if available, is pumped into the system from the inlet pipe 22 and added to the recovered flow going to the secondary drill hole 14. This additional water may also carry particulates. A filter (not shown) in the recirculated water pipe 24 removes the larger particles. It does not block the oil droplets or smaller particles. If the oil droplets are large enough or numerous enough, a substantial amount of oil will be returned to the ground. If the smaller particles are large enough or numerous enough, they will block up the holes in the seepage area 16. Neither condition is desirable. The detector of U.S. Pat. No. 4,381,674, assigned to Micro Pure Systems, Inc., and incorporated herein by reference, permits the identification and detection of the smaller solid particles, while the detector 30 of this invention permits the identification and detection of the oil droplets to determine the amount of oil in the recirculating oil flow.

In the preferred embodiment, ultrasonic transducer 32 operates generally as in U.S. Pat. No. 4,365,515, also incorporated herein by reference. The transducer 32 acts as a transmitter and sends pulses of ultrasonic energy into the recirculated water flow. Solid particles in the flow reflect this energy back, i.e., backscatter, to the first transducer 32. This backscattering may be detected by the transducer 32 and used to count and compute particle size, as explained in U.S. Pat. No. 4,381,674.

Unlike solid particles, however, oil droplets 48 in the flow also forward-scatter a portion of the ultrasonic pulse that hits them. Forward-scattering, which is shown in a simplified manner in FIG. 2, merely means that when the ultrasonic energy from the transducer 32 strikes the droplet, some portion of the ultrasonic energy radiates omnidirectionally, including in the forward direction away from the transmitting transducer 32. A forward-scattered signal from each droplet is then detected by the second transducer 36. In order to detect this forward-scatter and avoid any detection of backscatter signal, the second transducer 36 is optimally placed at an angle of at least 90° to the initial pulse. The number of such forward-scattered signals is counted by the pulse counter 42, which may be set to detect droplets only above a certain size. The raw count for a given time period or unit volume of flow is then compared with test data obtained for the particular system by running a sequence of tests with different levels of oil concentrations for the same time period or unit volume of flow. This comparison gives the amount of oil concentration in the flow.

OTHER EMBODIMENTS

Figure 3:
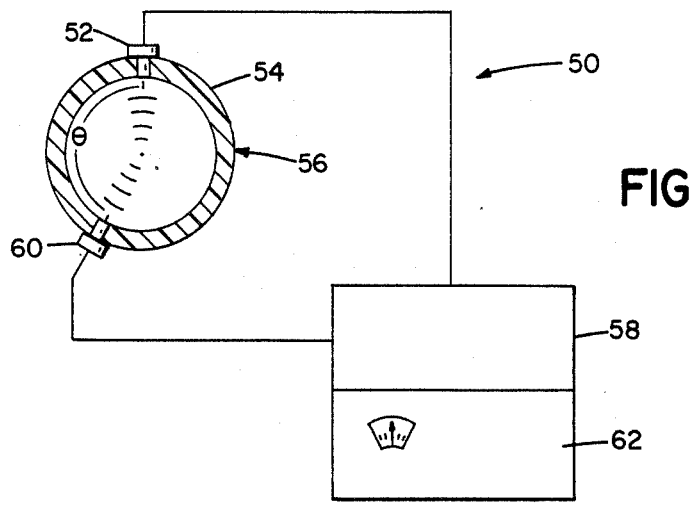
FIG. 3 is a block diagram of another preferred embodiment of the invention.

In another embodiment of this invention, the detector 50 of FIG. 3 is used. The detector 50 has a first transducer 52 mounted in the sidewall 54 of a recirculated water pipe 56. The transducer 52 is connected to a pulser-receiver 58 of the same type as the preferred embodiment. A second transducer 60 is also mounted in the sidewall 54. The angle shown is about 120°, although the 90° angle and other angles could be used as well. The second transducer 60 is also connected to the pulser-receiver 58, which is in turn connected to an absorption monitor 62. The absorption monitor is a MPA 1700, also available from Micro Pure Systems, Inc.

In operation, the first transducer 52 sends its pulses into the flow, a portion of which is detected by the second transducer 60. The output of the second transducer 60 is in the form of a voltage ($V_1$) to the pulser-receiver 58. The pulser-receiver compares this voltage ($V_1$) with an internal voltage standard (8 volts) from the absorption monitor 62 to produce an absorption value in decibels:

$$dB = 20 \log (V_1/8).$$

If oil droplets are present in the flow, the forward-scattering effect will add to that dB level as a sort of "oil gain". The relative value of this oil gain can be used by comparison to test data similar to the preferred embodiment to determine the oil concentration in the flow.

As also shown in FIG. 3, the two transducers 52, 60 have the same focal point in the flow. The focal points, however, could be different.

This method and apparatus may also be used with tertiary oil recovery systems and with systems having multicomponent flows where one element of the flow forward-scatters ultrasonic energy.

Other variations will occur to those skilled in the art.

What we claim is:

1. A method of identifying and determining the concentration of droplets in a fluid flow comprising:
   sending ultrasonic pulses into the flow,
   detecting and counting the resulting pulses of forward-scattered energy which occur when one of the ultrasonic pulses sent into the flow strikes a droplet in the flow, and
   comparing the number of forward-scattered energy pulses counted per unit volume of the flow with the number of forward-scattered energy pulses counted for known concentration levels of droplets for the same unit volume.

2. The method of claim 1 wherein said droplets are oil droplets, and the flow is a recirculating water flow for a secondary oil recovery system.

3. The method of claim 1 wherein said detecting includes detecting the pulses of forward-scattered energy at an angle equal to or greater than 90° from the direction at which said ultrasonic pulses are sent into the flow.

4. The method of claim 3 wherein said angle is 90°.

5. The method of claim 3 wherein said angle is 120°.

6. The method of claim 1 wherein said pulses are sent transversely across the flow.

7. A method of identifying and determining the concentration of droplets in a fluid flow comprising:
   sending ultrasonic pulses into the flow,
   detecting the amplitude of forward scattered energy which results when an ultrasonic pulse sent into the flow strikes a droplet in the flow,
   and comparing the detected amplitude with known applitudes to determine the concentration of droplets based on the amount of gain in the amplitude due to the forward-scattering.

8. The method of claim 7 wherein said droplets are oil droplets, and the flow is a recirculating water flow for a secondary oil recovery system.

9. The method of claim 7 wherein said detecting includes detecting the pulses of forward-scattered energy at an angle equal to or greater than 90° from the direction at which said ultrasonic pulses are sent into the flow.

10. The method of claim 9 wherein said angle is 90°.

11. The method of claim 9 wherein said angle is 120°.

12. The method of claim 7 wherein said pulses are sent transversely across the flow.

13. An apparatus for identifying and determining the concentration of droplets in a fluid flow comprising;

means for transmitting ultrasonic pulses into the flow, means for detecting and counting the discrete pulses of forward-scattered energy which results when an ultrasonic pulse from said means for transmitting strikes a droplet in the flow, and means for comparing the number of forward-scattered pulses counted per unit volume of flow with the number of forward-scattered pulses for known concentration levels of droplets for the same unit volume.

14. The apparatus of claim 13 wherein said means for detecting comprises a transducer disposed at an angle of at least 90° from the direction at which said ultrasonic pulses are sent into the flow.

15. The apparatus of claim 13 wherein the droplets are oil and the fluid is a secondary oil recovery system.

16. An apparatus for identifying and determining the concentration of droplets in a fluid flow comprising:

means for transmitting ultrasonic pulses into the flow, means for detecting the amplitude of forward-scattered energy which results when an ultrasonic pulse sent into the flow strikes a droplet in the flow, and means for comparaing the detected amplitude with known amplitudes to determine the concentration of droplets based upon the amount of gain in the amplitude due to forward-scattering.

17. The apparatus of claim 16 wherein said means for detecting comprises a transducer disposed at an angle of at least 90° from the direction at which said ultrasonic pulses are sent into the flow.

18. The apparatus of claim 16 wherein the droplets are oil and the fluid flow is a secondary oil recovery system.

* * * * *